(12) United States Patent
Adlam et al.

(10) Patent No.: US 10,456,514 B2
(45) Date of Patent: Oct. 29, 2019

(54) CARDIAC ASSIST DEVICE

(71) Applicant: University of Leicester, Leicester (GB)

(72) Inventors: David Adlam, Leicester (GB); Samara-Ratna Piyal, Leicester (GB)

(73) Assignee: University of Leicester, Leicester (GB)

( * ) Notice: Subject to any disclaimer, the term of this patent is extended or adjusted under 35 U.S.C. 154(b) by 44 days.

(21) Appl. No.: 15/563,299

(22) PCT Filed: Apr. 1, 2016

(86) PCT No.: PCT/GB2016/050925
§ 371 (c)(1),
(2) Date: Sep. 29, 2017

(87) PCT Pub. No.: WO2016/156866
PCT Pub. Date: Oct. 6, 2016

(65) Prior Publication Data
US 2018/0071444 A1 Mar. 15, 2018

(30) Foreign Application Priority Data

Apr. 1, 2015 (GB) .................................... 1505624.5
Apr. 2, 2015 (GB) .................................... 1505765.6

(51) Int. Cl.
*A61M 1/10* (2006.01)
*A61M 1/12* (2006.01)

(52) U.S. Cl.
CPC ............ *A61M 1/122* (2014.02); *A61M 1/106* (2013.01); *A61M 1/1068* (2013.01); *A61M 1/1086* (2013.01); *A61M 1/107* (2013.01); *A61M 1/1058* (2014.02); *A61M 1/1096* (2014.02)

(58) Field of Classification Search
CPC ....................................................... A61M 1/10
See application file for complete search history.

(56) References Cited

U.S. PATENT DOCUMENTS

| 4,771,765 A | 9/1988 | Choy et al. |
| 5,169,378 A | 12/1992 | Figuera |

FOREIGN PATENT DOCUMENTS

| WO | WO-97014286 A2 | 4/1997 |
| WO | WO-00076288 A2 | 12/2000 |
| WO | WO-00078375 A1 | 12/2000 |
| WO | WO-02019917 A1 | 3/2002 |
| WO | WO-2004066805 A2 | 8/2004 |
| WO | WO-2007149562 A2 | 12/2007 |
| WO | WO-2008106420 A1 | 9/2008 |
| WO | WO-2009088916 A1 | 7/2009 |
| WO | WO-2013082505 A1 | 6/2013 |

OTHER PUBLICATIONS

Walvoort, Bert, "International Search Report," prepared for PCT/GB2016/050925, dated Sep. 2, 2016, seven pages.

*Primary Examiner* — Matthew W Schall
(74) *Attorney, Agent, or Firm* — Winstead PC

(57) ABSTRACT

A device for providing assistance to ventricular systole, the device comprising a pressuriser and a driver, wherein the pressuriser is adapted to be able to apply localised pressure to only the external wall of one ventricle, or a portion thereof, and the driver is operatively linked to the pressuriser so as to be able to drive a cycle of increased and decreased pressure applied by the pressuriser. The invention also relates to a method of implanting the device and a method of treating cardiac pump failure in which the device is used.

29 Claims, 13 Drawing Sheets

Upgraded Experiment Configuration

1.

Evacuated balloon
collapses into
diameter <6mm

2.

Deployed shape causes
outer ring to expand
into deployed state and
locates the device

3.

Central part of structure
inflates to actuate

B) Pump and Control System

CARDIAC ASSIST DEVICE

The present invention relates to a cardiac assist device for evaluating cardiac function, in particular a method that provides assistance to ventricular systole. The invention also relates to a method in which the aforementioned device may be used.

In the heart of a healthy individual, the amount of blood pumped from the ventricles is generally optimised (ie blood pumped from the left ventricle to the aorta and from there onto the rest of the body, and the right ventricle to the pulmonary artery and from there to the lungs). However, in many acute and chronic conditions the ability for the ventricular tissue to contract effectively is adversely affected, thereby leading to a reduction in the amount of blood that is able to be pumped from either or both ventricles (ie a reduction in the fraction of the amount of blood held in the ventricle that can be ejected during each period of systole; an inadequate cardiac output). As a consequence of this, the body is unable to provide sufficient oxygen via the blood to meet the demands of the body, leading to lethargy, shortness of breath and in some situations cardiac failure and/or other organ failure. For example, an acute condition that can lead to a reduction in the ability for the ventricles to pump (ie cardiac pump failure) is myocardial infarction. In such a condition, the cardiac pump failure may also be acute (ie cardiogenic shock or myocardial stunning), or chronic if the myocardial infarction leaves lasting damage to the ventricular tissue. Chronic conditions such as congestive cardiac failure can present with chronic cardiac pump failure.

Myocardial infarction is associated with considerably morbidity and mortality with 280,000 patients in the US alone reported to die from heart failure annually. When conditions such as this lead to an acute failure for one or both ventricles to pump, patients are often able to recover if they are provided with a temporary support during the early phase of the condition. Current medical interventions include the administration of intravenous inotropic agents. However, such agents increase the myocardial demand for oxygen and so can risk exacerbating myocardial injury and so increase the risk of catastrophic arrhythmia. An alternative to therapeutic agents is the use of cardiac assist devices. Such devices that are currently in clinical use work by passing blood out from the heart to a mechanical pump that is external to the heart. The pump then pumps the blood back to the heart, aorta or pulmonary artery. Such devices require significant surgery to put in place; often not ideal for patients that are already in a weak condition. When in place, such devices can be a route for infection and can act as a focus for coagulation (thereby risking thrombotic complications). Alternative devices have been considered, but none are thought to adequately direct the assisting of ventricular contraction to be of clinical value, and as a consequence no other form of device is known to be in clinical use.

5.1 million patients in the US alone are thought to live with chronic heart failure. Currently, the focus of treatment for this patient group is via administration of chemotherapeutic agents and by the controlling of the electrical activity of the heart (eg by implantation of a cardioverter defibrillator). In some cases, however, such treatments are unable to provide a good level of return towards normal cardiac function.

Consequently, there remains a need for further devices capable of assisting the function of a heart. Such devices would be particularly useful if they could operate without having to be included in the circulation of the cardiovascular system.

It has surprisingly been found that, if directed correctly, a pressure applied to the heart by a cardiac assist device can significantly improve the cardiac ejection fraction, without the need to implant a pump that is provided within the circulation of the cardiovascular system. Improvements of 10-20% in the ejection fragment is achievable by such a device, which is considered to provide a significant improvement in patient symptoms and outcomes for those with cardiac output deficit.

Accordingly, in the first aspect of the present invention, there is provided a device for providing assistance to ventricular systole, the device comprising a pressuriser and a driver, wherein the pressuriser is adapted to be able to apply localised pressure to only the external wall of one ventricle, or a portion thereof, and the driver is operatively linked to the pressuriser so as to be able to drive a cycle of increased and decreased pressure applied by the pressuriser.

The inventors have found that by applying pressure to the external wall of a ventricle, one can aid the ventricular tissue to decrease the size of the intra-ventricular cavity and so to increase the fraction of blood evacuated from the ventricle during systole to a significant degree; this being achieved without the need to employ a pump system within the circulation or to commit to surgery on the heart itself. It is however not as simple as applying a general external pressure to the heart. The inventors have found that to optimise this function, it is important that a pressuriser is operated under the direction of a driver and is adapted to apply localised pressure to only the external wall of one ventricle, or a portion thereof. Only pressure applied to a ventricle at the appropriate time to assist ventricular systole is able to make a significant difference to the amount of blood pumped around the body or to the lungs. It is also important to note that the left and right ventricles operate under very different pressures and may not enter and leave their period of systole at the same time. Consequently, it is important that the pressuriser is adapted so as only to be driven to apply pressure to the external wall of one ventricle; in this way the driving of the pressuriser can be organised to apply the optimal pressure during the optimum period for that ventricle (applying pressure at the same time to both ventricles cannot achieve the required optimisation). An added advantage of such a device is that a pressuriser, with or without a driver, may be manufactured in a size that enables percutaneous delivery to the pericardial space between the pericardium and the heart, something that is not possible when a pump is required.

The pressuriser may apply expansive or compressive pressure.

The pressure applied by the pressuriser may, for example, be from 0.5 to 2.0 N, from 0.75 to 1.75 N, from 0.75 to 1.5 N, from 0.75 to 1.25 N, or about 1 N.

The driver is any device that is able to direct the pressure cycles of the pressuriser. For example, the driver may be a computer operated pump, or a solenoid or piezoelectric actuator. The driver may be set to drive a preselected cycle (for example, 54 to 84 expansions or compressions per minute). However, in order to ensure most accurate application of the pressuriser during the appropriate period of the cardiac cycle the device may include a feedback mechanism.

For example, the device may further comprise a cardiac event timing sensor adapted so that in use the cardiac event timing sensor can distinguish between periods of ventricular systole and ventricular diastole, the cardiac event timing sensor being operatively linked to the driver such that when the device is in use the driver can direct an increase in the pressure to be timed in order to be applied by the pressuriser during the appropriate period of the cardiac cycle. The person skilled in the art would be able to determine what period during the cardiac cycle would be appropriate for applying ventricular pressure. For example, this period may be ventricular systole, or may be during ventricular systole, for example during peak ventricular systole, during early systole (eg during the first 1, 5, 10 or 15% of the period of systole) and/or during late systole (eg during the last 1, 5, 10 or 15% of the period of systole). However, the period may not be restricted to this period, for example, the appropriate period could be at the beginning of ventricular diastole (eg during the first 1, 5, 10 or 15% of the period of diastole). Optionally, for example, the cardiac event timing sensor is adapted so that in use it can identify peak ventricular systole and so the driver can direct an increase in pressure to be timed in order to be applied by the pressuriser ruing the period of peak ventricular systole.

The skilled person would be aware of a number of clinical tools that can be used in order to determine periods of systole and/or diastole for a ventricle, and so that would be useful as a cardiac event timing sensor in the context of the present invention. For example, an ECG, which provides an electrocardiagraphic measurement of the electrical functioning of the heart. The skilled person is well aware what electrical events provided in an ECG correspond to systole, and so how to determine from an ECG the period of systole for the left or right ventricle. For example, the QRS complex may be considered to coincide with the period of systole. The T-wave may be considered to coincide with the period of diastole.

When the cardiac event timing sensor is an ECG it may detect electronic signals from the cardiac cycle to enable the driver to direct an increase in pressure to be timed in order to be applied by the pressuriser during appropriate period in the cardiac cycle In this way the cardiac event timing sensor and the driver act together to form an ECG gate system.

In order to complete the cycle, and in order to optimise the ability for the ventricle to fill with blood, the cardiac event timing sensor may be able to direct the driver to drive a decrease in pressure to be timed in order to be applied by the pressuriser during periods that are appropriate for ensuring adequate ventricular filling (which in turn assists with the optimisation of cardiac output). The person skilled in the art would be able to determine what period during the cardiac cycle would be appropriate for a decrease in pressure. For example, this period may be ventricular diastole, or may be during ventricular diastole, for example during peak ventricular diastole, and/or during late diastole (eg during the last 1, 5, 10 or 15% of the period of diastole). Optionally, the cardiac event timing sensor is adapted so that in use it can identify the appropriate period during the cardiac cycle in which to apply a decrease in ventricular pressure. For example, peak ventricular diastole may be identified and so the driver can direct a decrease in pressure to be timed in order to be applied by the pressuriser during the period of peak ventricular diastole.

During periods of reduction in the pressure applied to the ventricle, the pressure applied by the pressuriser may be reduced to below 0.5 N, optionally to about 0 N. Whilst the pressure applied by the device may be reduced during the cycle of increased and decreased pressure applied by the pressuriser, in some instances the pressure may not be eliminated entirely, consequently, during periods of a reduced pressure, a pressure may still be applied, for example, the pressure may not be reduced below 0.1, 0.2, 0.3, 0.4, 0.4 or 0.5 N.

The device may be adapted to direct a number of forms of cycling of increased and decreased pressure. For example, the driver of the device may include control circuitry adapted to direct the driving of an increase of pressure by the pressuriser to be timed to coincide with every appropriate period for applying ventricular pressure, every second such period, or every third such period. For example, every systolic event, every second systolic event or every third systolic event. The driver of the device may include control circuitry adapted to direct the driving of a decrease of pressure by the pressuriser to coincide with every appropriate period for a decrease in pressure, every second such period or every third such period. For example, every diastolic event, every second diastolic event, or every third diastolic event.

The inventor has surprisingly found that the anatomy around the heart provides a convenient place to position the device in order to optimise its function. The heart is surrounded by a substantially inelastic double layered fibroserous sac called the pericardium. There is a relatively small potential space between the pericardium and the heart into which the device of the present invention is optimally placed. When in this position, the device may be braced between the pericardium and the outer wall of a ventricle. Consequently, when pressure is applied by the pressuriser to the external wall of a ventricle, the device is braced against the unyielding surface of the pericardium, thereby assisting to direct pressure to the relatively elastic ventricular wall.

The device according to the present invention is configured to take advantage of the above dynamics.

Accordingly, the pressuriser may for example comprise, or is, an expandable member. On expansion within the pericardium, after the potential space between heart and pericardium has been filed, the expandable member is only permitted to expand further by expanding in the direction of the relatively flexible ventricular wall.

The expandable member itself may have an external surface with a non-uniform expandability that enables it to expand preferentially in one direction. For example, the external surface may comprise two principle faces provided on substantially opposite sides of the expandable member. The surface of a first face permitting less or no expansion compared to the second face. This may be facilitated by the first face being made from a less elastic material than the second face, or from a non-elastic material. Alternatively, or additionally, this may be facilitated by the first face being supported by or fixed to a rigid support surface, into which the expandable member may not expand. The second face may be expandable so as to form a convex profile in the direction away from the first face. When a ventricle is not operating correctly, it is not able to contract to the correct form required to eject blood from its cavity. The shape of the face of the second face of the expandable member is configured to enhance the ejection of blood from the ventricle. The first face may be substantially planar. In this way, when provided between the pericardium and the ventricle, and the device is implanted so that the first face is directed towards the pericardium and presents a surface to be braced against the pericardium, and the second face is directed towards the ventricle, the expandable member will preferentially therefore expand in the direction of the ventricle presenting a rounded bulge into the ventricular wall. The first face is optionally broad relative to the second face.

The pressuriser may comprise more than one expandable member. In such a configuration, the pressuriser may comprises a first portion, in which is located a first expandable member, supported on a second portion, in which is located a second or more expandable members. The first expandable member may be any one of those described above. When the first expandable member is expandable so as to form a convex profile, the convex profile extends away from the second portion. The first expandable member may be operatively linked to the driver.

The first expandable member of the first portion may be supported directly on the second or more expandable members. The first expandable member may be secured to the second or more expandable members. Alternatively, a support may be provided between the first and second portion, the expandable members may be secured to the support. If more than two expandable members are included, the two or more expandable members may be juxtaposed to each.

In use, the second or more expandable members may present a first face (optionally substantially planar) to the pericardium with a second and substantially opposed face (optionally being substantially planar) towards the first portion of the pressuriser. The first face of the second or more expandable member is optionally broad relative to the surfaces of the first expandable member. In order to optimise controllability of the device, it has been found that it is best for the second or more expandable members to expand into the potential space between the ventricle and the pericardium, but not to expand to apply any significant pressure to the ventricle. It is then the expansion and contraction of the first expandable member as described above that directly results in a cycle of pressure changes on the ventricle wall.

Consequently, the second or more, or combination of the second and more, expandable members may take up a larger volume when in expanded form than that of the first expandable member.

When the pressuriser comprises more than one expandable member, the first expandable member may have a maximum cross-section dimension when in expanded form of from 1.5 cm to 3 cm, and a minimum cross-section dimension of from 1.5 to 3 cm. The second expandable member may have a maximum cross-section dimension when in expanded form of from 5 to 10 cm, and a minimum cross-sectional dimension of from 5 to 10 cm.

The second and more expandable members may not be required to undergo cycles of expansion or contraction, as it may only be required to be expanded during placement, and thereafter only potentially require change of this expansion if further expansion is require to counteract natural expansion of the space between pericardium and heart over time, or for removal when contraction of the expandable member is required. Consequently, the second and more expandable members may not be linked to the driver and cardiac event timing sensor described above. However, if more than two expandable members are provided in the second portion, their relative level of expansion may be controlled during deployment in order to control the angle at which the first expandable member in the first portion that is supported above the second portion is presented to the ventricle wall.

Consequently, the second and more expandable members of the second portion of the pressuriser may be adapted to permit control of their relative amount of expansion and shape of expansion so as to direct the presentation angle of the first expansion member. This control may be virtue of a second driver system with control circuitry adapted to direct the driving of the expansion of each expandable member in the second portion of the pressuriser, or by manual expansion of the expandable members (eg during deployment).

An example of a device according to the present invention is one where the pressuriser comprises a first portion, in which is located a first expandable member, supported on a second portion, in which is located a second expandable member. The first expandable member comprises two principle faces provided on substantially opposite sides of the first expandable member. The surface of a first face permitting less or no expansion compared to the second face. The second face may be expandable so as to form a convex profile in the direction away from the first face. The second expandable member has a first substantially planar face that is provided on the side opposed to the first expandable member. The second expandable member may have a larger volume when in expanded form than that of the first expandable member.

In a further example of a device according to the present invention, there is provided a device wherein the pressuriser comprises a first portion in which is located a first expandable member and a second portion in which is provided a second expandable member, when both expandable members are expanded the first expandable member forms an annular ring defining a membrane with the second expandable member expanding in the centre of the ring and in a direction that is opposed to the membrane. In use, the first expandable member of the device expands against the pericardium, whilst the second expandable member expands against the ventricle.

The device of the present invention may further include a support structure for the expandable member that is in the form of fingers arranged in a circle and that splay outwardly from the centre of the circle. The fingers may also be outwardly arching. In such a form, the fingers from a cupped cavity, from the centre of which the expandable member may expand braced against the fingers. In use the fingers extend through a surgical opening in the pericardium and their splayed arrangement facing the ventricle forms a stop-projection that prevents the extraction of the device back through the pericardium, whilst at the same time provide a rigid or semi-rigid surface in association with the pericardium from which the expandable member may brace itself during expansion. The expandable member may be any of the first expandable members discussed above. In undeployed form the expandable member is provided in unexpanded form and within a substantially tube-shaped structure formed by the fingers. In such a form the fingers are straight and not outwardly splayed. The fingers of the device may be made from shape-memory wire, that takes the form of the deployed form when cold, but the un-deployed form when heated.

The pressuriser may apply expansive pressure via an expandable member that is in the form of a balloon. Consequently, any of the expandable members described above may be a balloon.

However, any form that is capable of providing expansive pressure within the requirements of the present invention may be used as part of the present invention. For example, the expandable member may include an arm capable of extending from the device (eg urged by a solenoid or piezoelectric device). The arm may be extended to and from the ventricular wall in order to apply or relieve pressure to the wall. The device will also then require a stop-projection from the device that is able to brace the device between a fixed surface and the extending arm. In use, for example, a radially extending flange from the device may abut with the internal wall of the pericardium, preventing the device from returning through the surgically induced hole in the pericardium used to implant the device whilst also bracing the device between the pericardium and the extending arm. The arm may terminate in a substantially planar plate in order to distribute the pressure applied by the arm to the wall of the ventricle.

As an alternative to the pressuriser providing expansive pressure via one or more expandable members, the pressuriser may provide pressure via compression of the ventricular wall.

For example, the pressuriser may comprise radially extending fingers that can define a first circumference in one position, but when pressure is to be applied a second position is taken where the fingers are closed together forming a second circumference that is smaller than the first. When the fingers are urged into abutment with a portion of the ventricular wall, the wall buckles between the fingers during operation, thereby applying compressive pressure to the ventricular wall.

Any of the devices of the present invention may include a fastener that enables the device to be attached to the external wall of the ventricle. The fastener may, for example, be a rough surface that can releasable secured to the ventricular tissue. The fastener may be in the form of hooks. The fastener may be provided on the surface of the pressuriser, in particular the surface that when in use faces the ventricle.

The devices of the present invention may be supplied without a driver, for attachment to a driver when in use. Consequently, the devices of the present invention may be any of those described above without a driver (or cardiac event timing sensor).

Any of the devices of the present invention may be used in any of the following methods of implanting a cardiac assist device or in methods of treating cardiac pump failure.

A method of deploying the cardiac assist device of the present invention includes the installation of the device via the apical route through a surgery created opening in the pericardium, such that the device can be braced between the pericardium and the external wall of only one ventricle. Delivery may be by the seldinger technique.

The present invention also encompasses a method of treating cardiac pump failure in a subject by operating any one of the above-mentioned cardiac assist devices so as to apply localised pressure to only the external wall of one ventricle, or a portion thereof, in the subject in a cycle of increased and decreased pressure. The control of the cycle is directed to optimise the cardiac output and so may be in response to the feedback mechanism discussed above with reference to ECG. Cardiac pump failure may be as a result of myocardial infarction, cardiogenic shock and/or myocardial stunning.

The present invention will now be described, by way of example, with reference to accompanying figures, in which:—

1. EX-VIVO TESTING OF THE DEVICES OF THE PRESENT INVENTION

Figure 1A:
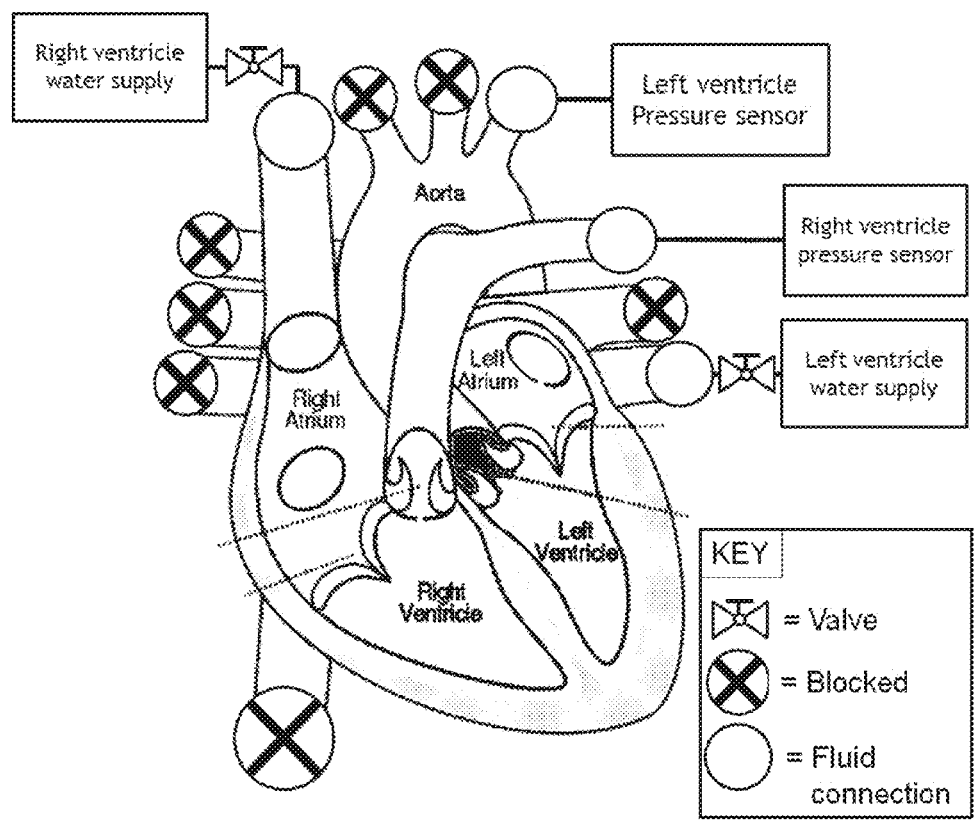
FIG. 1A illustrates an isolated pig heart.
Figure 1B:
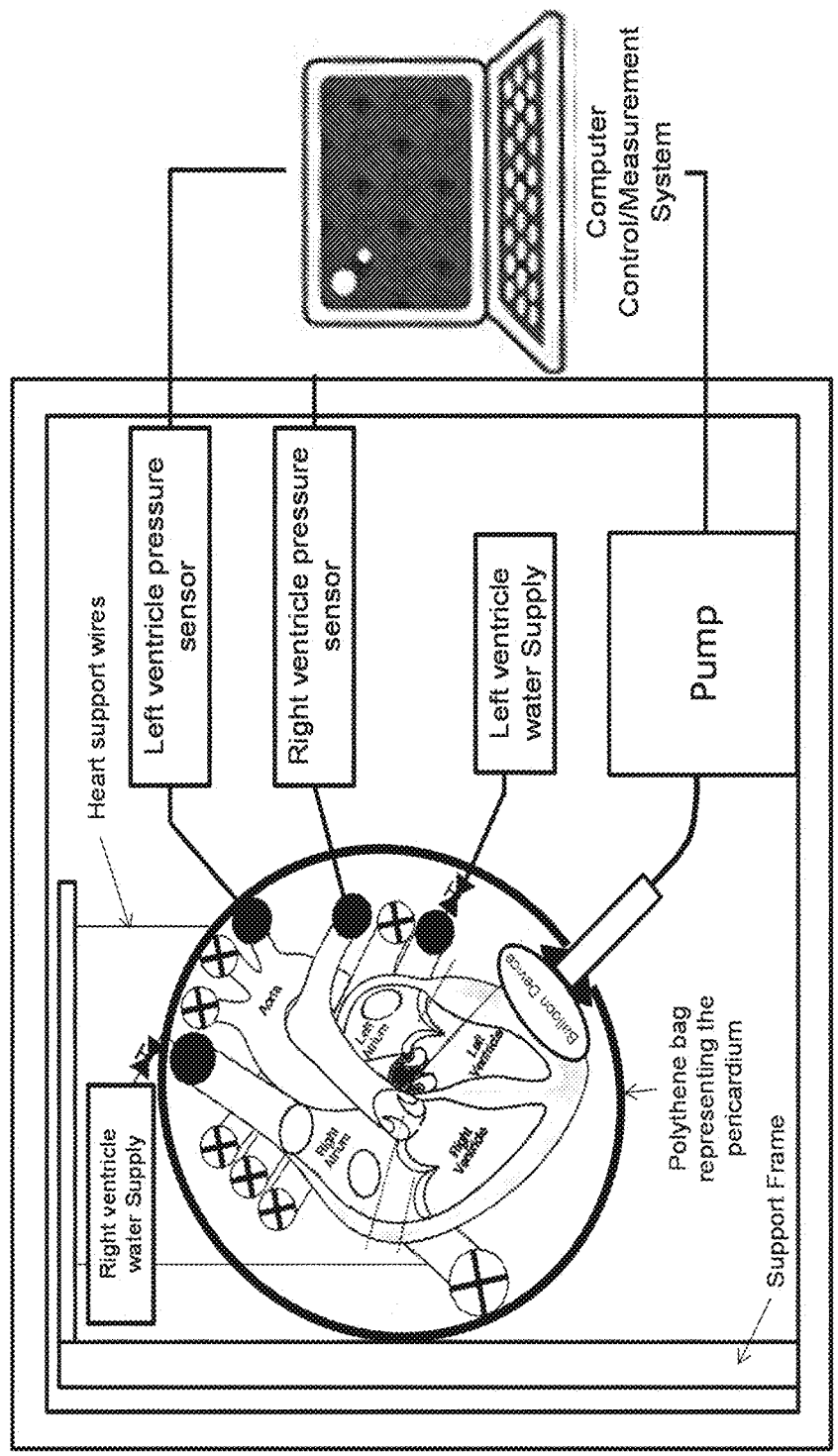
FIG. 1B illustrates the isolated pig heart set-up to demonstrate the devices of the present invention.

An isolated pig heart was prepared for analysis by being filled with water via valves provided in the superior vena cava and the pulmonary vein (see Right ventricle water supply and Left ventricle water supply in FIG. 1), whilst pressure sensors were positioned at the left subclavian artery and at the left pulmonary artery (see left ventricular pressure sensor and right ventricular pressure sensor in FIG. 1). The remaining lumens to and from the heart were blocked. Water was supplied to the heart until the pressure detected at the pressure sensors indicated that the pressure achieved was similar to that during normal heart function (about 80 mmHg). The heart prepared in this manner was supported by support wires and relatively tightly contained within a polythene bag. The polythene bag is an inelastic material and represents the pericardium. A device according to the present invention that includes a balloon was inserted through a hole in the polythene bag so as to be braced between the left ventricle of the isolated pig's heart and the polythene bag. Expansion and contraction of the balloon was controlled by a pump that was externally provided to the polythene bag and that itself was under the control of a computer-control system.

When the balloon was inflated by the pump a force against the external wall of the left ventricle was exerted by the balloon (itself being braced against the inner inelastic wall of the polythene bag) which was demonstrated to cause a pressure rise within the heart that was measured by the pressure sensors. The pressure rise is a direct measure of the magnitude of assistance provided by the device to the contraction of ventricular muscle.

Tests provided on the above set-up have demonstrated that the cardiac assist devices according to the present invention are able to consistently provide assistance to the function of the heart over a length of time.

Figure 2:
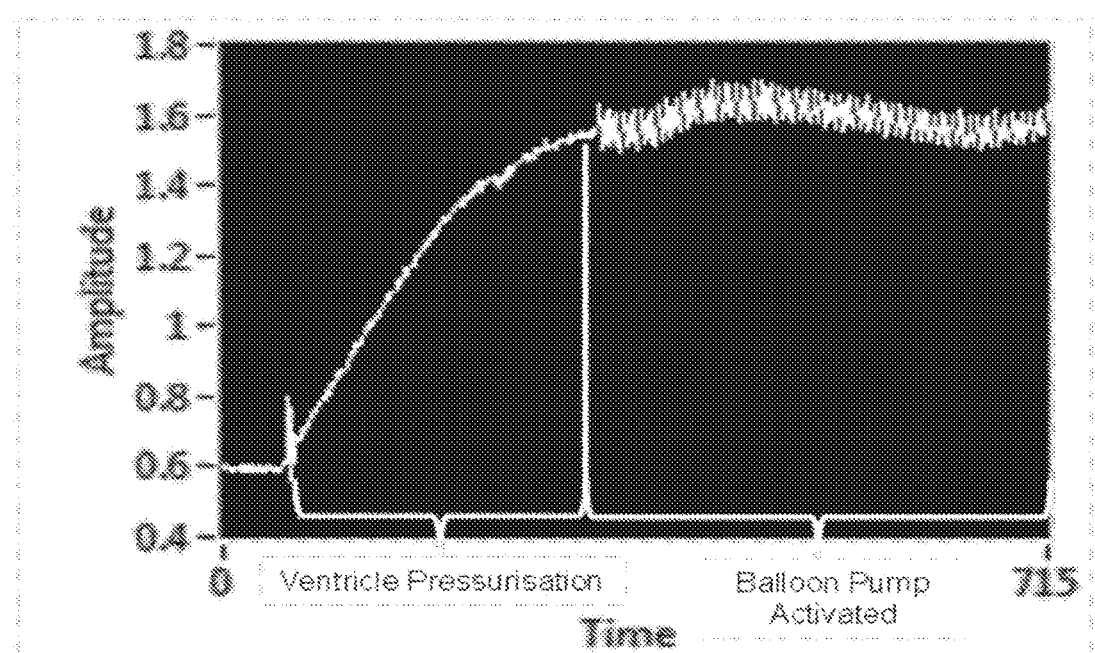
FIG. 2 shows pressure responses from an isolated pig heart when activating a device according to the present invention and as tested in the set-up of FIG. 1.

FIG. 2 shows the pressure identified at the sensors of the set-up of FIG. 1 (the X-axis) over time (Y axis) as the isolated pig's heart is set up. During the initial period of ventricular pressurisation the pressure can be seen to gradually rise as the heart is filled with water, until the pig's heart is filled to a pressure that is close to the target pressure of 80 mmHg ("ventricular pressurisation"). Once reaching this target pressure the pump is driven by the computer control system to apply 84 expansions per minute of the balloon, thereby applying repeated cycles of expansion of the balloon and so pressure on the left ventricle 84 times a minute. As can be seen from FIG. 2, this produces a regular short rise and fall in pressure during the period in which the pump is activated to inflate the balloon by the computer control system.

Figure 3:
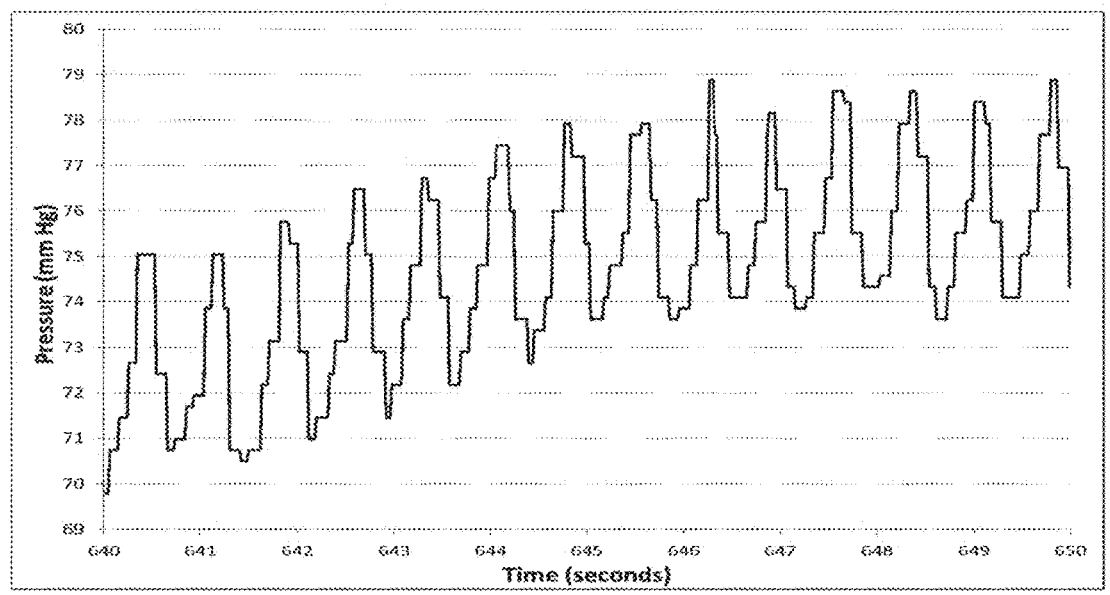
FIG. 3 shows the pressure response from an isolated pigs heart when activating a device according to the present invention at 84 expansions per minute and using the set-up of FIG. 1.

FIG. 3 provides more detailed analysis of the period during the balloon pump activation. It can be seen that there is a relatively consistent increase in pressure spikes achieved with each balloon expansion when the device is run on an 84 expansions per minute protocol. The increase in pressure with each expansion equates to about a 12.5% assistance to the ventricular contraction.

Figure 4:
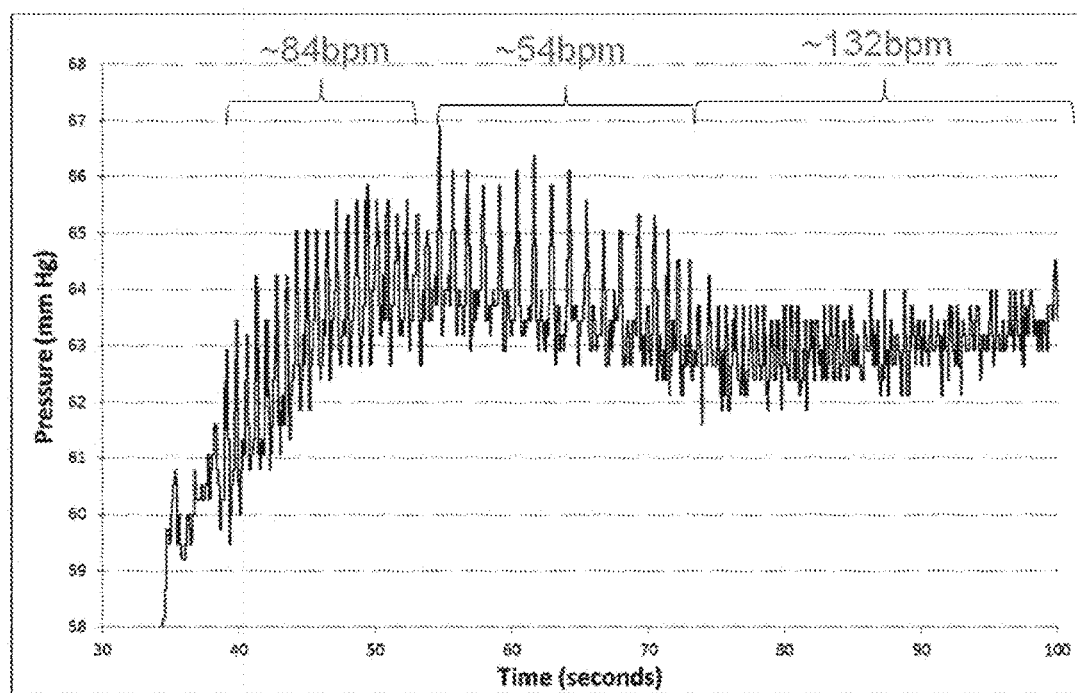
FIG. 4 shows a pressure response from an isolated pig heart when activating a device according to the present invention under conditions of varying expansion rates and using the set-up of FIG. 1.

The computer control system was then used to drive the pump in a manner that changed the number of expansions per minute (bpm) of the balloon over time. It can be seen in FIG. 4 the results of running the balloon on an 84 expansion per minute protocol, followed by 54 expansion per minute protocol and finally an approximately 132 expansion per minute protocol. It is clear from these results that the device would be able to respond to physiologically relevant changes in heart rate.

Figure 5:
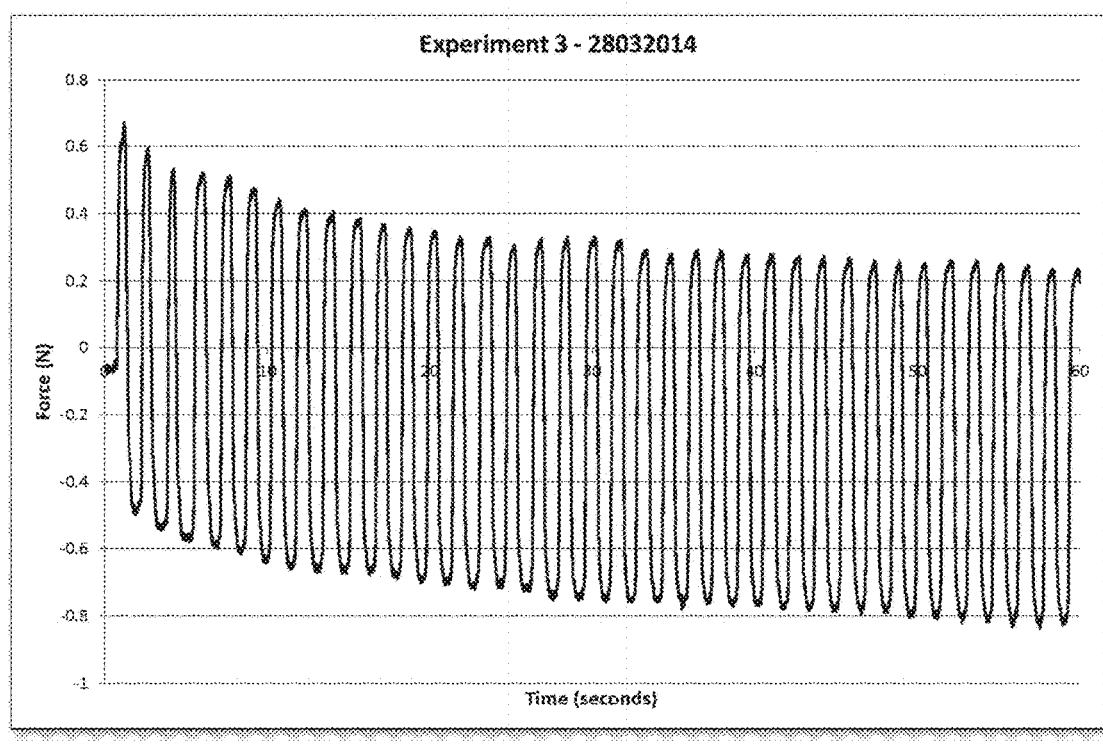
FIG. 5 shows the force applied by the device in a modified set up of that illustrated in FIG. 1 where the isolated pigs heart is exchanged for a pressure sensor.

In order to get a clearer understanding of the level of assistance provided by the device of the present invention in assisting ventricular systole, the set-up of FIG. 1 was altered by replacing the heart with a force measurement sensor. The force measurement sensor was modified with a custom manufactured plate installed to mimic the shape of the left ventricle. When the balloon was placed against the portion of the plate that took the form of the left ventricle within the polythene bag, the operation of the device is able to apply a force on the plate in the same manner as it had to the heart, but in this case the precise force applied may be measured. Results of the balloon being operated under a protocol of about 37 expansions per minute are provided in FIG. 5. As can be seen from FIG. 5, approximately one newton force was consistently generated by the balloon during this test on each expansion. This is thought to be equivalent to about 20% of heart assistance at a rate sufficient to aid patient recovery.

2. OPERATION OF A MULTI-BALLOON DEVICE

Figure 6:
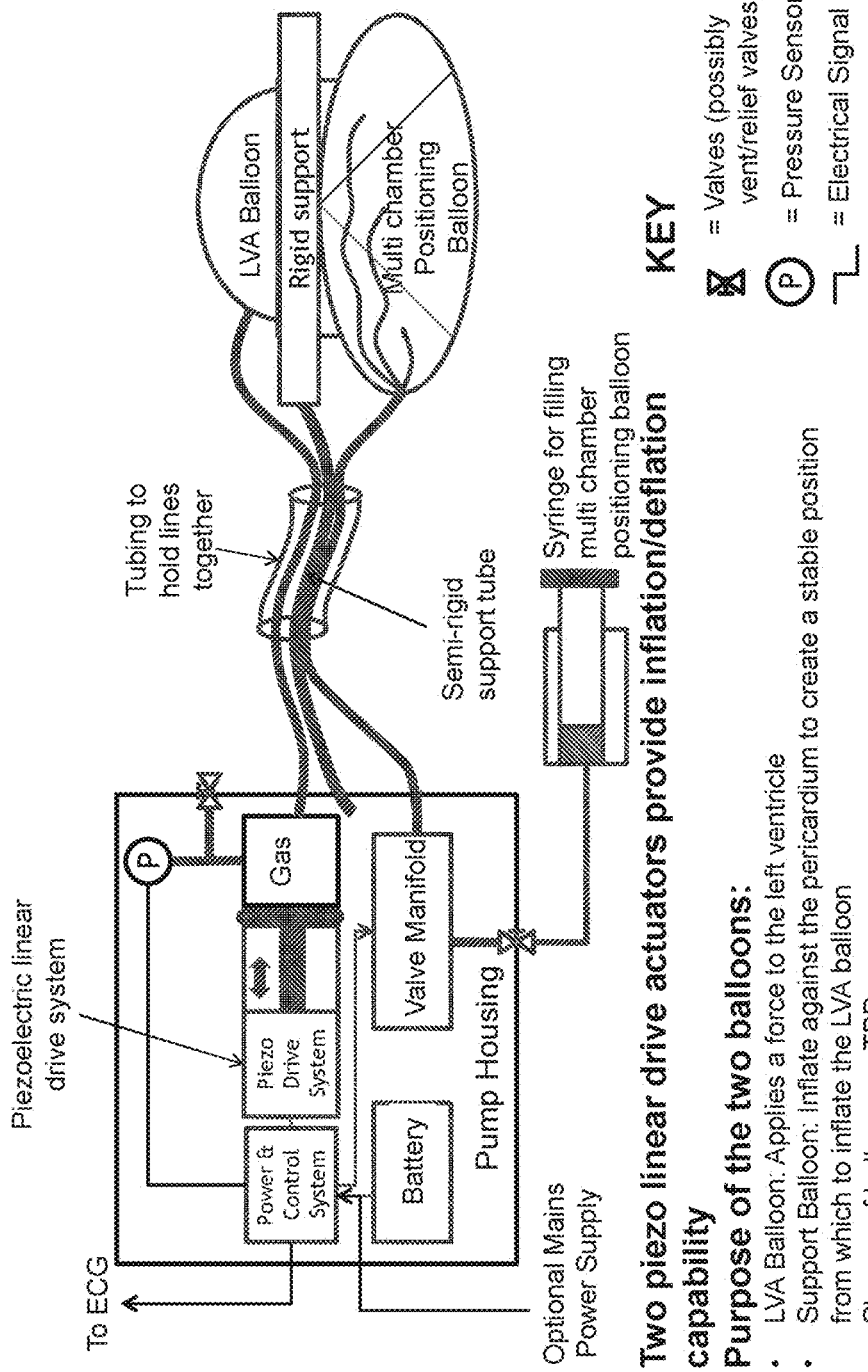
FIG. 6 shows an embodiment of the device of the present invention including details of an ECG gate system.

FIG. 6 provides a schematic for the operation of a multi-balloon device according to the present invention. In this embodiment, the device includes a left ventricular assist balloon (LVA balloon) separated from a multi chamber positioning balloon by a rigid support. The LVA balloon expansion cycles are controlled by a ECG gate system. This gate system includes a piezo driver that pushes gas in or draws gas away from the LVA balloon in order to power expansion and contraction of the balloon. As this is controlled in response to the ECG analysis the expansion and contraction of the LVA balloon can be co-ordinated to the beats of the heart in order to apply pressure to the left ventricle at the appropriate period of the cardiac cycle. The multi-chamber positioning balloon system may operate in isolation from the LVA balloon as expansion of the multi-chamber positioning balloon may be operated by a syringe via valve manifold. The multi-chamber positioning balloon may, for example, be inflated manually shortly after implantation to the patient in order to achieve expansion of the multi-chamber positioning balloon so as to fill the potential space between the pericardium and ventricular wall. Thereafter, the multi-chamber positioning balloon may be left inflated with only the inflation levels of the LVA balloon altered by the aforementioned drive system so as to apply the required cycles of pressure to the left ventricular wall.

3. AN EMBODIMENT OF A DOUBLE BALLOON DEVICE ACCORDING TO THE PRESENT INVENTION

Figure 7:
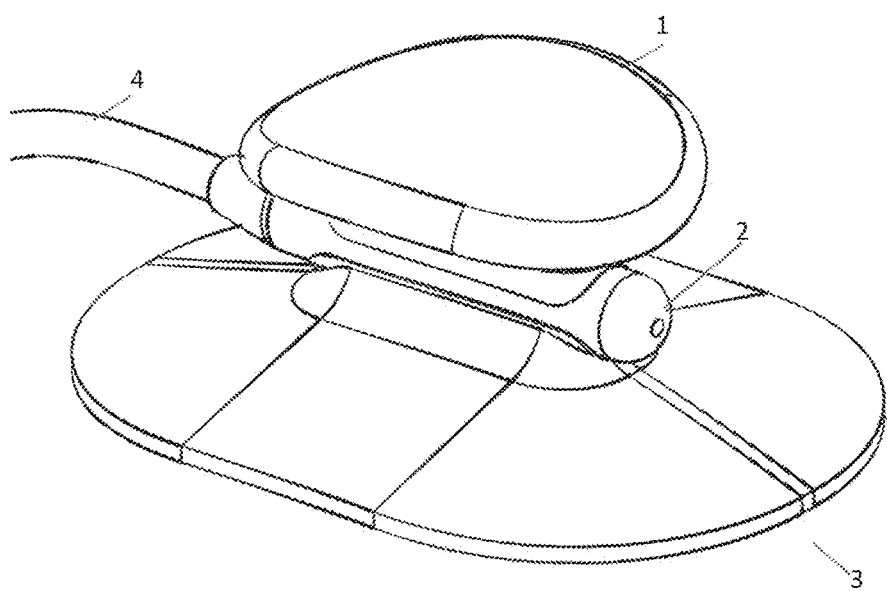
FIG. 7 shows an embodiment of the device of the present invention that utilises two expandable members.

A double balloon device according to the present invention is illustrated in FIG. 7. In this embodiment a first balloon (1) is connected to a delivery hub (2) with a second balloon (3) also being connected to the delivery hub (2). The first and second balloons (1, 3) are provided on opposite sides of the delivery hub (2). The device is shown in deployed form. In this form it can be seen that the second balloon (3) presents a first face as a broad substantially planar surface with a second substantially opposed face facing towards the first balloon (1). In use, the substantially planar first face of the second balloon (3) would be placed against the pericardium. The first balloon (1) in expanded form expands to extend away from the second balloon (3) so as to form a convex profile. Expanding to form a convex profile forms a rounded bulge that in use applies pressure into the ventricular wall. Attached to the delivery hub (2) is a supply conduit (4). A tubing (not shown) for each of the balloons (1, 3) is transmitted through the supply conduit (4) to the delivery hub (2) and from there to each of the balloons (1, 3). A fluid (gas or liquid) may be transmitted back and forward independently along each of the tubing in order to inflate or deflate the balloons (1,3).

4. SINGLE BALLOON EMBODIMENT OF THE PRESENT INVENTION

Figure 8:
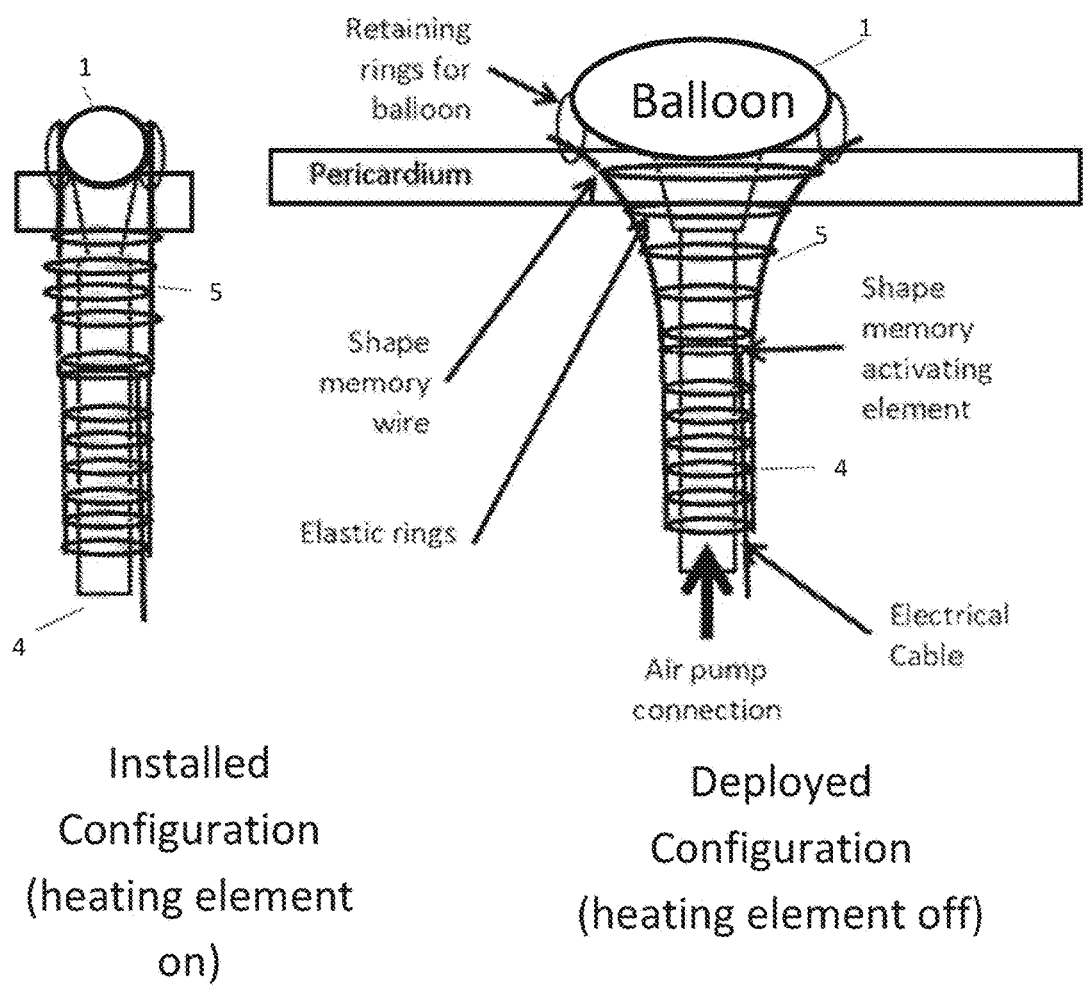
FIG. 8 shows an embodiment of the device of the present invention that utilises a single expandable member.

FIG. 8 illustrates one form of the present invention where a single balloon is employed. The illustration on the right-hand side of FIG. 8 shows the device in a deployed format. This device includes fingers (5) that are arranged in a circle and splay in an arch outwardly from the centre of the circle. In such a form, the fingers form a cupped cavity, from the centre of which the balloon (1) expands braced against the fingers. Elastic rings around the periphery of the circle formed by the fingers (5) urge the fingers (5) together and away from their natural splayed out position. In use, the fingers (5) extend through a surgical opening in the pericardium and a splayed arrangement facing the ventricle forms a stop-projection that prevents the extraction of the device back through the pericardium, whilst at the same time providing a rigid or semi-rigid surface in association with the pericardium from which the balloon (1) may brace itself during expansion. The balloon is retained to the fingers (5) by rings.

Expansion of the balloon (1) is achieved by air being pumped through the supply conduit (4).

The pre-deployed format (or format ready for extraction) of the device is shown in the illustration on the left-hand side of FIG. 8. In this format the balloon is collapsed and the fingers brought substantially together. The fingers are formed from a shaped memory wire which when heated by the action of an electrical cable conform to the shape on the left-hand side of the figure, but in the absence of heat via electrical cable the fingers conform to the shape shown on the right-hand side of FIG. 8.

5. NON-BALLOON EMBODIMENT OF THE DEVICE

Figure 9:
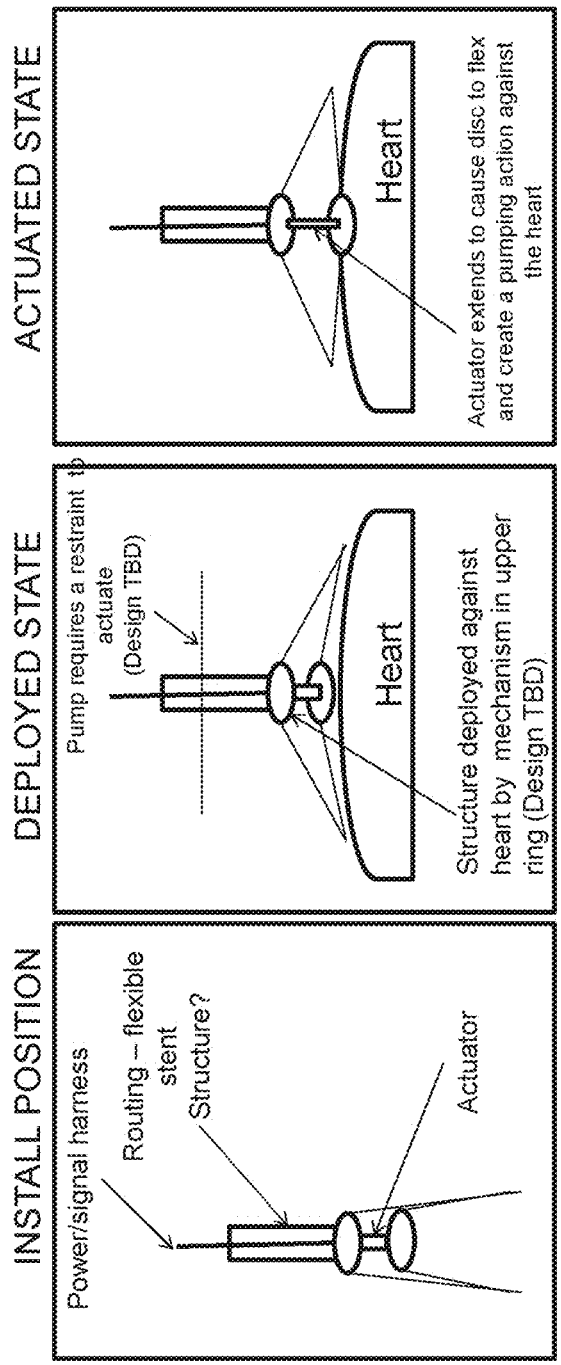
FIG. 9 shows an embodiment of the device of the present invention that utilises an expandable arm as an expandable member.

FIG. 9 shows an embodiment of the present invention in a configuration suitable for use during installation, in a configuration suitable for being deployed when in position and in a configuration when deployed and applying pressure to the ventricle (ie actuated state). This embodiment of the present invention does not include a balloon. Instead, the device includes an arm (6) that extends from the device after being urged by a solenoid or piezoelectric device. At the end of the arm is a substantially planar plate (7) which, in use, is forced against the surface of the ventricle by the extension of the arm (6) and thereby applies pressure to the ventricular tissue. In order that this pressure applied to the ventricular wall is braced against a fixed surface, the device includes a ring (8) that operates as a stop-projection from the device. In use, when the device is deployed within the pericardial space the ring (8) abuts with the pericardium, preventing the device from returning through the surgical induced hole in the pericardium used to implant the device, whilst also bracing the device between the pericardium and the extending arm (6).

6. ALTERNATIVE DOUBLE-BALLOONED DEVICE

Figure 10:
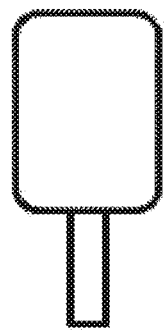
FIG. 10 shows an alternative embodiment of the device of the present invention that utilises two expandable members.
Figure 10:
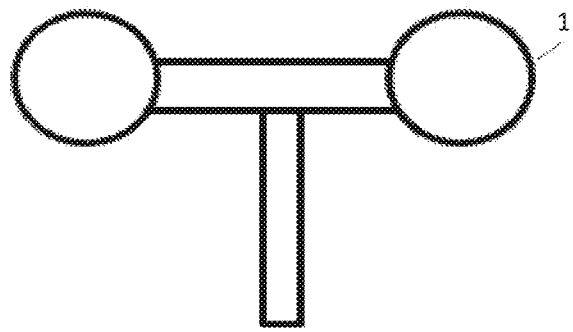
Figure 10:
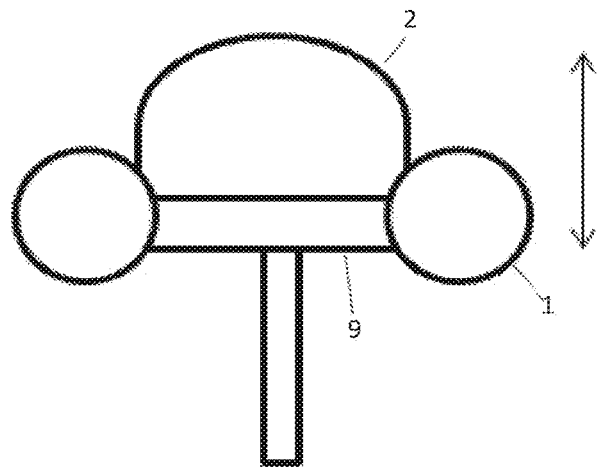

FIG. 10 illustrates an alternative double-balloon device. In the deployed position, the device includes a first balloon (1) and a second balloon (2), when both balloons are expanded the first balloon (1) forms an annular ring defining a membrane (9) with the second balloon (2) expanding in the centre of the ring (1) and in the direction that is opposed to the membrane (9). In use, the first balloon (1) of the device expands against the pericardium, whilst the second balloon (2) expands against the ventricular wall.

7. DEVICE IN SITU

Figure 11:
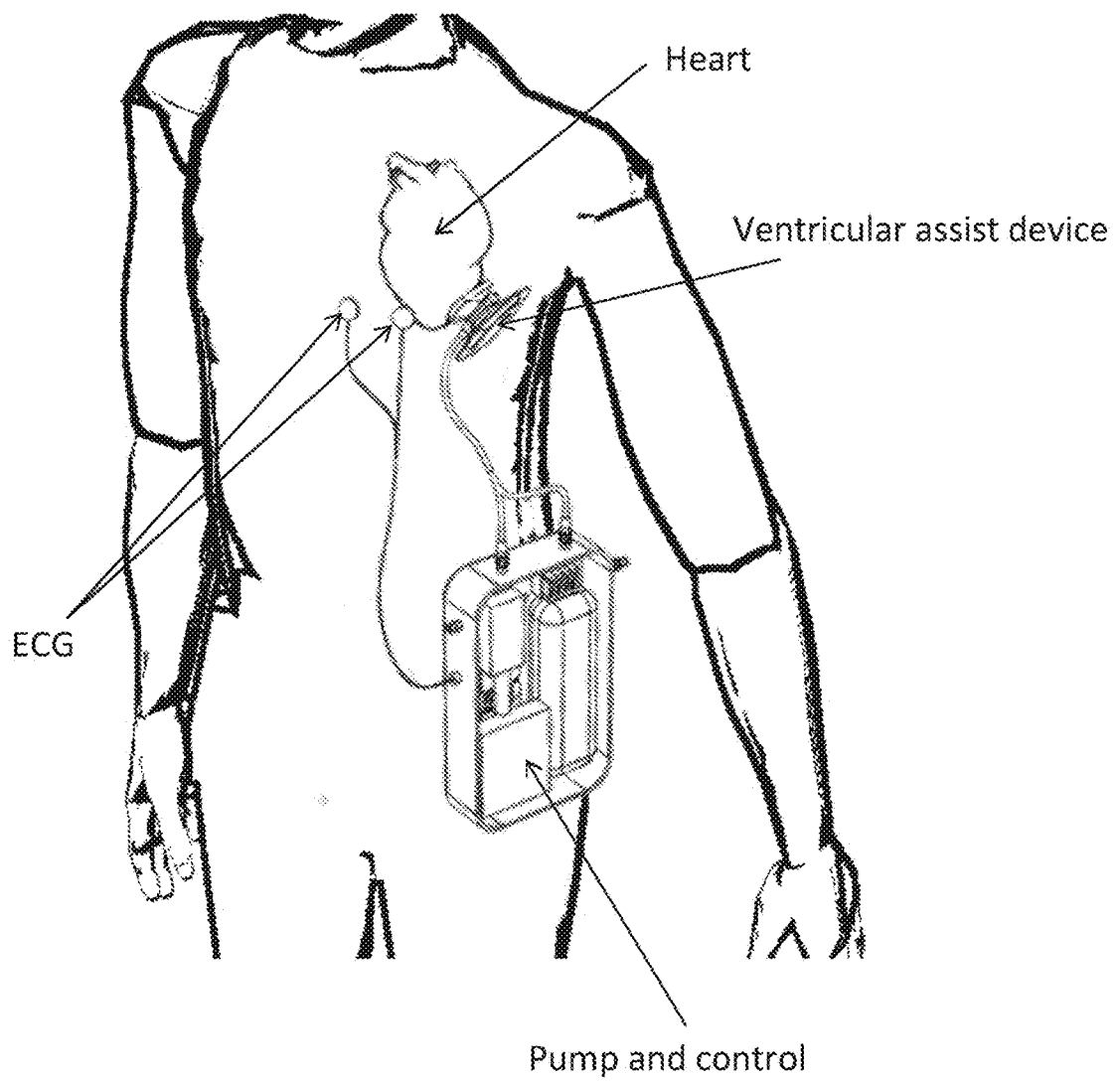
FIG. 11 shows the device of the present invention in position when in use.
Figure 12:
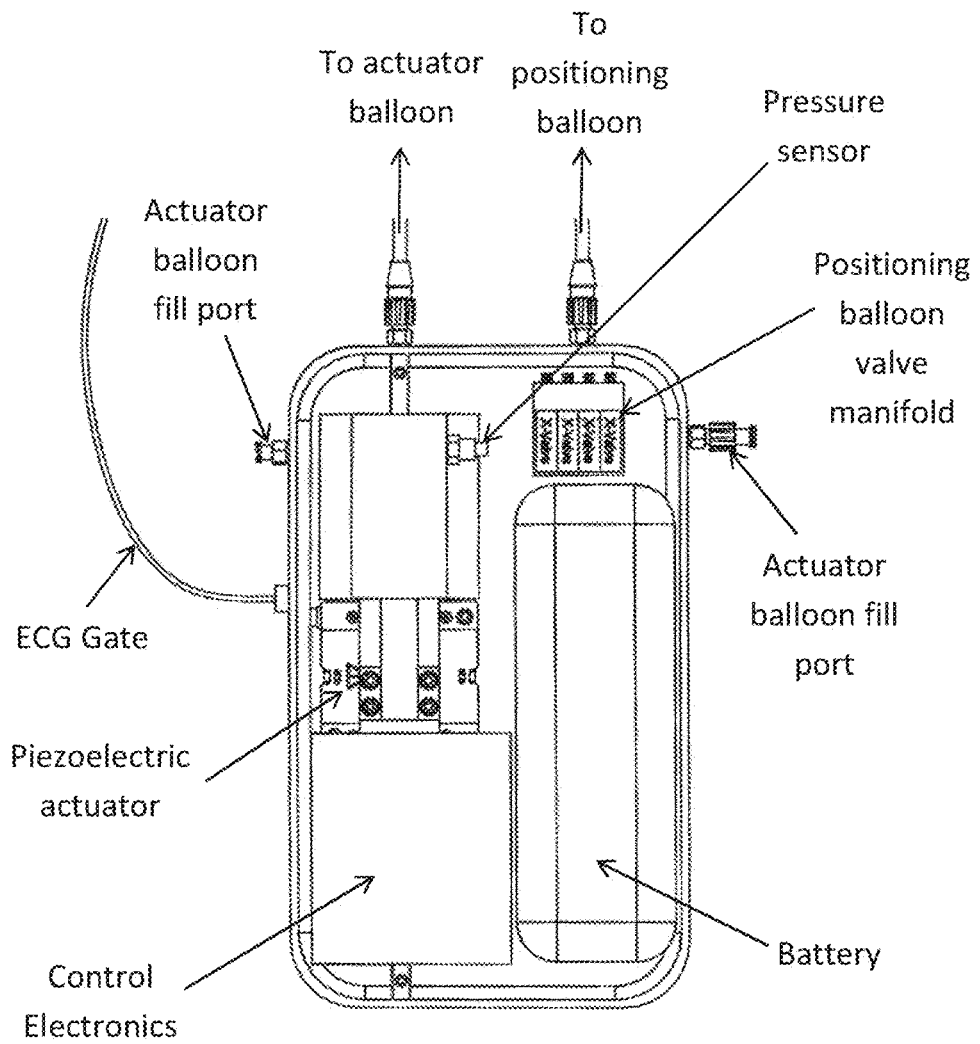
FIG. 12 shows the pump and control system of the device of the present invention.

The device in situ is illustrated in FIG. 11. In particular, FIG. 11 shows the device of FIG. 7 in place against the left ventricle and connected to a pump control system that is external to the body. Cutaneously applied ECG probes that feed back to the pump and control system are also shown. FIG. 12 provides further detail of the pump and control system.

The invention claimed is:

1. A device for providing assistance to ventricular systole of a heart, the device comprising:
   a pressurizer;
   a driver;
   wherein the pressurizer is adapted to apply localized pressure to only the external wall of one ventricle or a portion thereof;
   wherein the driver is operatively linked to the pressurizer to drive a cycle of increased and decreased pressure applied by the pressurizer; and
      wherein the device is braced between the pericardium and the outer wall of a ventricle during use.

2. The device as claimed in claim 1, further comprising a cardiac event timing sensor adapted so that in use the cardiac event timing sensor can distinguish between periods of ventricular systole and ventricular diastole.

3. The device as claimed in claim 2, wherein the cardiac event timing sensor is operatively linked to the driver such that when the device is in use the driver can direct an increase in the pressure to be timed in order to be applied by the pressurizer during the appropriate period of the cardiac cycle for assisting ventricular systole.

4. The device as claimed in claim 2, wherein the cardiac event timing sensor is operatively linked to the driver such that when the device is in use the driver can direct a decrease in pressure to be timed in order to be applied by the pressurizer during periods that are appropriate for ensuring adequate ventricular filling.

5. The device as claimed in claim 2, wherein the cardiac event timing sensor comprises an ECG.

6. The device as claimed in claim 1, wherein the pressure applied by the pressurizer is from 0.5 to 2.0 N.

7. The device according to claim 1, wherein the driver includes control circuitry adapted to direct the driving of an increase of pressure by the pressurizer every appropriate period for applying ventricular pressure to assist ventricular systole, every second such period, or every third such period.

8. The device according to claim 1, wherein the driver includes control circuitry adapted to direct the driving of a decrease of pressure by the pressurizer every appropriate period for ensuring ventricular filling, every second such period or every third such period.

9. The device according to claim 1, wherein the pressurizer is, or comprises, an expandable member.

10. The device according to claim 9, where the expandable member is a balloon.

11. The device according to claim 9, wherein the expandable member has an external surface with a non-uniform expandability that enables it to expand preferentially in one direction.

12. The device as claimed in claim 11, wherein the external surface of the expandable member comprises two principle faces provided on substantially opposite sides of the expandable member, the surface of a first face permitting less or no expansion compared to the second face, the second face permitting expansion so as to form a convex profile in the direction away from the first face.

13. The device as claimed in claim 9, wherein the pressurizer comprises a first portion, in which is located a first expandable member, supported on a second portion, in which is located a second or more expandable member.

14. The device as claimed in claim 13, when more than two expandable members are included, the two or more expandable members are juxtaposed to each.

15. The device as claimed in claim 13, wherein the second or more expandable members presents a first face with a second and substantially opposed face towards the first portion of the pressurizer, the first face of the second or more expandable member is optionally broad relative to the surfaces of the first expandable member.

16. The device as claimed in claim 13, wherein the second or more, or combination of the second and more, expandable members may take up a larger volume when in expanded form than that of the first expandable member.

17. The device as claimed in claim 13, wherein when the first expandable member is expandable so as to form a convex profile, the convex profile extending away from the second portion.

18. The device as claimed in claim 13, wherein the, or only the, first expandable member is operatively linked to the driver.

19. The device as claimed in claim 13, wherein the second and more expandable members are adapted to permit control of their relative amount of expansion and shape of expansion so as to direct the presentation angle of the first expansion member.

20. The device as claimed in claim 13, wherein the pressurizer comprises a first portion in which is located a first expandable member and a second portion in which is provided a second expandable member, when both expandable members are expanded the first expandable member forms an annular ring defining a membrane with the second expandable member expanding in the center of the ring and in a direction that is opposed to the membrane.

21. The device as claimed in claim 9, further comprising a support structure for the expandable member that is in the form of fingers arranged in a circle and that splay outwardly from the center of the circle so as to form a cupped cavity, from the center of which the expandable member may expand braced against the fingers.

22. The device as claimed in claim 9, wherein the expandable member comprises an arm capable of extending from the device and a stop-projection from the device that when in use is able to brace the device between a fixed surface and the extending arm.

23. The device as claimed in claim 1, wherein the pressurizer comprises radially extending fingers that define a first circumference in one position, but when pressure is to be applied a second position is taken where the fingers are closed together forming a second circumference that is smaller than the first.

24. A device for providing assistance to ventricular systole, the device comprising a pressurizer that includes a first portion, in which is located a first expandable member, supported on a second portion, in which is located a second expandable member, the first expandable member comprising two principle faces provided on substantially opposite sides of the first expandable member, the surface of a first face permitting less or no expansion compared to the second face, the second face being expandable so as to form a convex profile in the direction away from the first face, the second expandable member having a first substantially planar face that is provided on the side opposed to the first expandable member, wherein the device is braced between the pericardium and the outer wall of a ventricle during use.

25. The device as claimed in claim 24, wherein the second expandable member has a larger volume when in expanded form than that of the first expandable member.

26. A device for providing assistance to ventricular systole, the device comprising a pressurizer that includes a first portion in which is provided a first expandable member and a second portion in which is provided a second expandable member, when both expandable members are expanded the first expandable member forms an annular ring defining a membrane with the second expandable member expanding in the center of the ring and in a direction that is opposed to the membrane, wherein the device is braced between the pericardium and the outer wall of a ventricle during use.

27. A device for providing assistance to ventricular systole, the device comprising an expandable member and a support structure, the support structure for the expandable member taking the form of fingers arranged in a circle and that splay outwardly from the center of the circle so as to form a cupped cavity, from the center of which the expandable member may expand braced against the fingers, wherein the device is braced between the pericardium and the outer wall of a ventricle during use.

28. A method of deploying the cardiac assist device of claim 1, wherein the method comprises the steps of the installation of the device through a surgery created opening in the pericardium, such that the device is braced between the pericardium and the external wall of only one ventricle.

29. A method of treating cardiac pump failure in a subject by operating any one of the cardiac assist devices of claim 1 so as to apply localized pressure to only the external wall of one ventricle, or a portion thereof, in the subject in a cycle of increased and decreased pressure.

* * * * *